(12) United States Patent
Altendorf et al.

(10) Patent No.: US 6,722,881 B1
(45) Date of Patent: Apr. 20, 2004

(54) PNEUMATIC-ELECTRIC CONVERTER FOR DENTAL INSTRUMENTS

(75) Inventors: Hans-Walter Altendorf, Worms (DE); Karl-Heinz Lehmann, Bensheim (DE)

(73) Assignee: Sirona Dental Systems GmbH (DE)

( * ) Notice: Subject to any disclaimer, the term of this patent is extended or adjusted under 35 U.S.C. 154(b) by 128 days.

(21) Appl. No.: 10/070,822

(22) PCT Filed: Sep. 11, 2000

(86) PCT No.: PCT/DE00/03150

§ 371 (c)(1),
(2), (4) Date: Mar. 11, 2002

(87) PCT Pub. No.: WO01/19276

PCT Pub. Date: Mar. 22, 2001

(30) Foreign Application Priority Data

Sep. 10, 1999 (DE) .......................... 199 43 474

(51) Int. Cl.⁷ ................................................ A61C 1/00
(52) U.S. Cl. ......................................................... 433/101
(58) Field of Search ............................. 433/27, 28, 98, 433/99, 100, 101, 103, 114; 318/551

(56) References Cited

U.S. PATENT DOCUMENTS

| 3,732,622 A | * | 5/1973 | Rackson ....................... 433/27 |
| 3,902,247 A | * | 9/1975 | Fleer et al. ................... 433/98 |
| 3,994,069 A | * | 11/1976 | Hohmann .................... 433/101 |
| 4,316,130 A | * | 2/1982 | Louarn ......................... 318/551 |

FOREIGN PATENT DOCUMENTS

DE  24 17 890  10/1975

\* cited by examiner

*Primary Examiner*—Ralph A. Lewis
(74) *Attorney, Agent, or Firm*—Dykema Gossett PLLC

(57) ABSTRACT

A dental device having at least one pneumatically operable handpiece, the rotational speed of which can be influenced by a control element designed as a foot-operated switch, and a further handpiece, which can be driven by means of an electric drive, and the compressed air present at the pneumatic handpiece influences the control of the electric drive. A graduated filter is mounted on a pneumatically actuated hollow body and the graduated filter has regions thereon which can be sensed by a light barrier generating an electric signal in dependence on the properties of the regions.

11 Claims, 4 Drawing Sheets

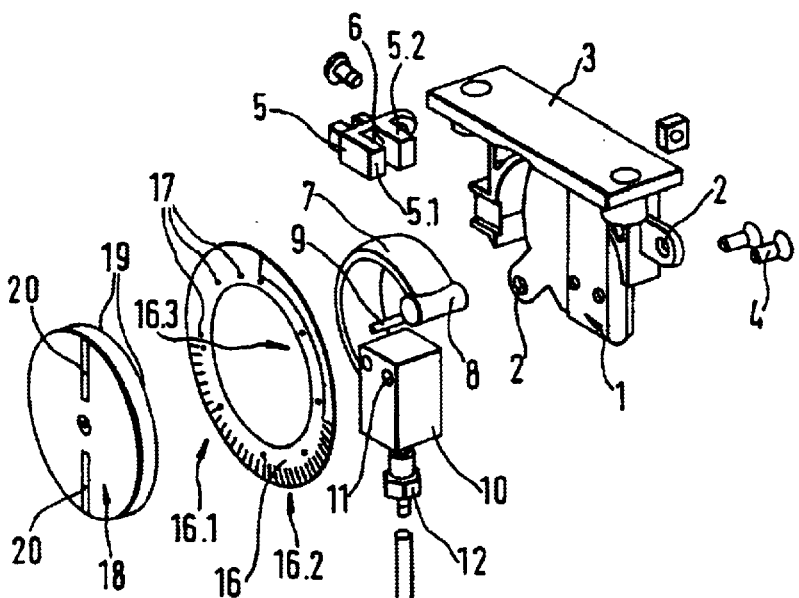
Fig.1
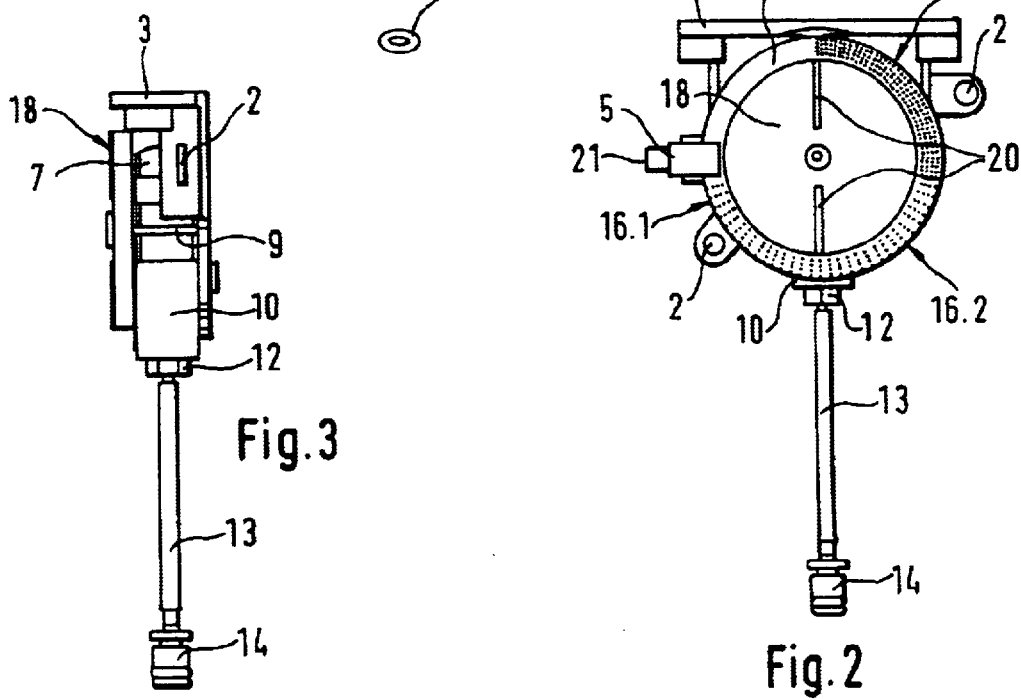
Fig.3
Fig.2

PNEUMATIC-ELECTRIC CONVERTER FOR DENTAL INSTRUMENTS

BACKGROUND OF THE INVENTION

The invention relates to a dental device having at least one electrically operable handpiece, the rotational speed of which can be influenced by a control element designed as a pneumatic foot-operated controller, the compressed air present at the output of the pneumatic control element influencing the control of the electric drive.

German published patent application DE 24 17 890 discloses a dental device in which at least one dental handpiece is connected to a compressed-air motor drive fed from a compressed-air source via a compressed-air line. The rotational speed can be changed by means of a control valve, controlling the compressed air, via a pneumatic control device, preferably designed in the form of a foot-operated switch. When using a further handpiece with an electric motor drive, which can be switched on and off via an electrical switching element and the rotational speed of which can be controlled by means of an electric control element, pressure converters are installed which control the compressed air controlled by the control valve for the compressed-air motor drive in such a way that an electric control element of the electric motor drive is influenced. The rotational speed is varied at the electric motor drive via an electric control element taking the form of a sliding contact.

It has be found that, in the case of pneumatic dental appliances which can be influenced in rotational speed by means of foot-operated control, the displacement to be completed at the foot-operated switch to bring about a corresponding change in rotational speed at the dental handpiece is greater at low pressures. However, this only relates to pneumatically operable dental handpieces. At greater pressures, a small change in displacement at the foot-operated switch is already sufficient to bring about a change in the rotational speed at the dental handpiece to be pneumatically operated. The subjective perception of the dentist on which this response is based can only be approximated by a non-linear characteristic, which is therefore also desirable for electrically operable handpieces.

To arrive at a characteristic with such a profile, which cannot be readily realized for example with pressure transducers available for purchase, electronic components (microprocessors, non-linear analog circuits) would therefore have to be used to convert the signal. The dentist would like to operate the electrically operable handpieces likewise with the pneumatic foot-operated control, so that it must be ensured that the rotational speed behavior of the electrically operable handpieces corresponds to the pneumatically operable handpieces, so that the dentist can ideally operate both handpieces by means of his accustomed way of operating the foot-operated control, irrespective of whether a pneumatically operable handpiece or an electrically operable handpiece is concerned.

SUMMARY OF THE INVENTION

The invention is based on the object of converting the signal of a pneumatically actuated foot-operated control in such a way that the electrically operable handpieces behave in a way proportional to a pneumatically driven handpiece.

This object is achieved according to the invention by providing that a dental device with at least one electrically operable handpiece, for which it is intended that the rotational speed can be influenced by a foot-operated controller and for which the compressed air downstream of the control element influences the control of the electric drive, is equipped with a graduated filter which is held on a pneumatically actuated hollow body, the graduated filter having formed on it regions which can be sensed by a light barrier generating an electric signal in dependence on the properties of the regions.

With the solution according to the invention, operation both of a pneumatically drivable handpiece and of an electrically drivable handpiece using a foot-operated control shared by both can be brought about, both the response of the pneumatically drivable handpiece and the response of the electrically drivable handpiece being made, by changes in the displacement at the foot-operated switch, to simulate the subjective perception of the dentist approximated best by a non-linear characteristic. Small changes in current intensity, and consequently small changes in rotational speed, at the electrically drivable handpiece can be realized, in the case of low pressures and great displacements at the foot-operated switch, by means of a p/I analog transducer.

In an advantageous way, the graduated filter is designed as a transmission disk. This disk, divided into sectors of different surface finishes, may for example have been provided with a different degree of blackening in each of its three or more sectors. As a result, different optical densities, lying between 0 and 4, can be realized. The degrees of blackening can be brought about for example by using a laser to work on the transmission disk serving as the graduated filter.

In a further refinement of the idea on which the invention is based, the pneumatically actuable hollow body is designed as a hollow spring, to the spindle of which the transmission disk can be fastened. The pneumatically actuable hollow body is part of a p/I analog transducer, the pressure chamber of which may have a connection to the hollow body, which may be designed as a hollow spring. The flexible hollow spring makes it possible to produce a deflection of the graduated filter about its spindle corresponding to the pressure in the p/I transducer. This deflecting movement of the graduated filter is sensed by a light barrier, which encloses the edge, and consequently the sectors provided with different surface finishes, of the graduated filter. Depending on the deflection of the graduated filter about its spindle, the light barrier detects a certain sector region, so that an electric signal corresponding to this sector region can be generated by the light barrier.

A likewise disclosed method of controlling the rotational speeds, on the one hand of an electrically drivable dental handpiece and on the other hand of a pneumatically drivable dental handpiece, which can both be held on a dental appliance and can be regulated in their rotational speed via a shared foot-operated control, comprises the following method steps:

applying the driving-air pressure to the input of the p/I analog transducer, deflecting a graduated filter by deforming a sensing the deflection of the graduated filter by a light barrier which is assigned to the latter and generates an electric signal, and determining the current intensity [1] of the current [I]/ pressure [p] characteristic.

By means of the method disclosed according to the invention, the electric drive of the electrically operable handpiece can be controlled via the foot-operated control with a response which corresponds to that of the pneumatically drivable handpiece which can likewise be activated via the foot-operated control.

In the range of driving-air pressures of 0 to 1 bar, the current intensity which can be preset at the electric drive increases proportionately more weakly than in the case of driving-air pressures at the p/I transducer which lie above a pressure of 1 bar.

BRIEF DESCRIPTION OF THE DRAWING

The invention will be explained more detail below with reference to a drawing, in which:

FIG. 1 is an exploded view of a p/I analog transducer according to the invention;

FIG. 2 is a front view of the p/I transducer of FIG. 1;

FIG. 3 is a side view of the p/I transducer according to FIG. 2;

DETAILED DESCRIPTION OF THE INVENTION

Figure 4:
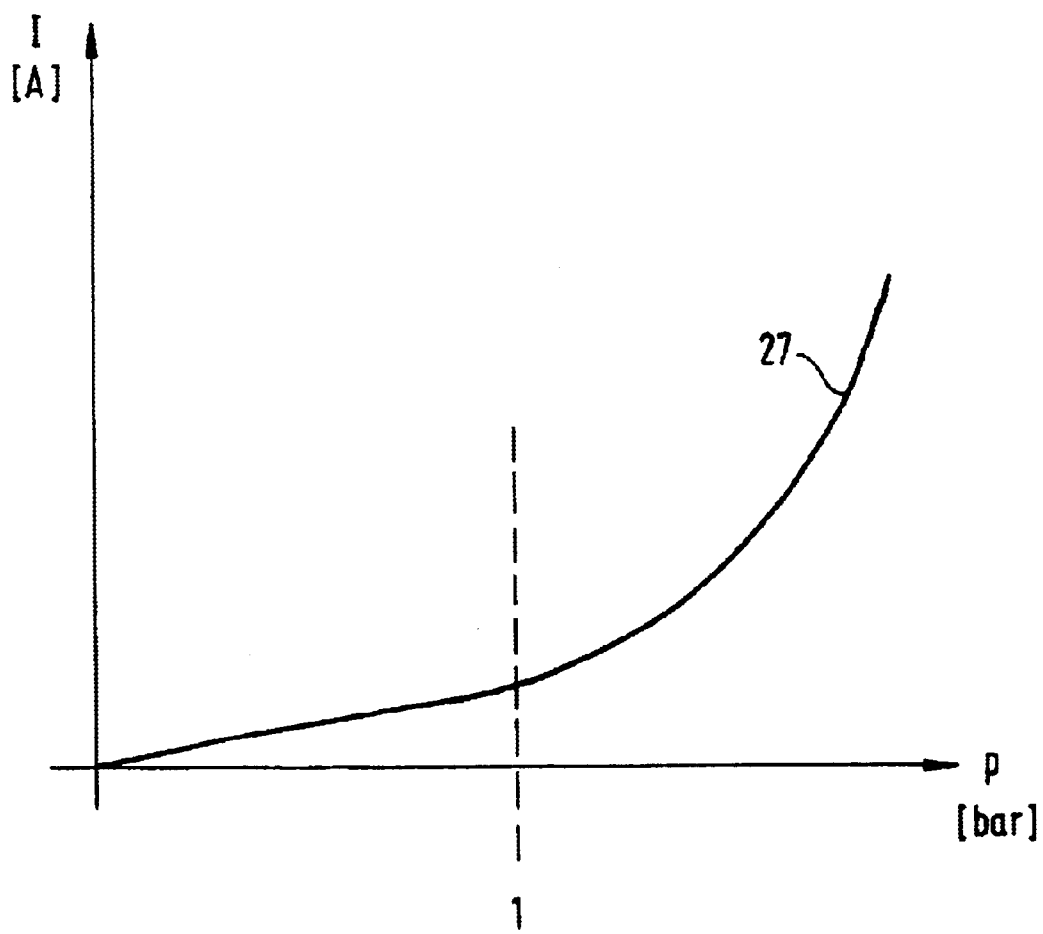
FIG. 4 is a graphic illustration of the desired progressive current [I]/pressure [p] characteristic.

The p/I analog transducer according to the invention shown in FIG. 1 includes a held plate-shaped terminating part provided on a support part 1 above fastening holes 2. The support part 1 of a pressure gage can be fastened to the associated panel by means of bolts 4. In the support part 1 there are two holes, through which the bolts 4 are inserted in order to fasten a part defining a pressure chamber 10 of a p/I analog transducer to the support part 1. From the pressure chamber 10 of the p/I analog transducer there extends a pneumatically actuable hollow body 7, which is designed in the embodiment of FIG. 1 as a hollow spring. The flexible hollow spring 7 opens out into a pressure body 8, on the front side of which a spindle 9 is fastened. The indicating disk 18 together with the graduated filter 16 fastened thereto are held on the spindle 9.

Beneath the pressure chamber 10 of the p/I analog transducer, a hose 13 is connected by means of a screwed inlet joint 12 to the pressure chamber 10, which is provided at its lower end with a nipple 14 together with a sealing ring 15. The driving-air pressure present in the pneumatic pressure supply system is applied to the pressure chamber 10 via the hose line 13.

The deflection of the graduated filter 16 fastened to the spindle 9 of the pneumatically actuable hollow body 7 is sensed by means of a light barrier 5, which embraces a clearance 6 between a first leg 5.1 and a second leg 5.2. The graduated filter 16—a transmission disk in the exemplary embodiment indicated—is divided into a plurality of different sectors 16.1, 16.2 and 16.3. Instead of the three sectors 16.1, 16.2 and 16.3 represented here, a greater number of sectors may also be formed on the periphery of the transmission disk 16. The sectors 16.1, 16.2 and 16.3 may cover, for example, a range of 10° to 170° at the beginning of the transmission disk 16 and have an optical density increasing in this range from 0 to 4.

The pressure chamber 10 of the p/I analog transducer measures a driving-air pressure in the range between 0 and 4 bar and can be loaded with 6 bar. The range of rotational speed at the dental handpiece for this pressure range lies between 0 and 40,000 rpm.

The light barrier 5 encloses the edge region of the graduated filter 16 with a first leg 5.1 and a second leg 5.2, between which the clearance 6 lies. The beam emanating from the light barrier 5 may be, for example, an infrared beam of a wavelength of 935±5 nm. The infrared beam is attenuated displacement-dependently by the sector 16.1 or 16.2 or 16.3 passing the clearance 6. The displacement-dependent attenuation can be realized, for example, by the sectors 16.1, 16.2 and 16.3 being provided with different degrees of blackening, which can be achieved for example by using a laser to work on the transmission disk 16. The surface finish of the sectors 16.1, 16.2 and 16.3 can also be provided with different roughnesses or the sectors may be made to have a different material thickness, which could likewise be sensed by a light barrier 5.

The transmission disk 16 serving as the graduated filter is provided with individual holes 17, into which pins 19 of an indicating disk 18 engage. On the front side, the indicating disk 18 is provided with a scale 20.

The line 13 shown in FIG. 2, extending up to the pressure chamber 10 from below, applies the blowing air pressure to the pressure chamber 10. This has the effect that the actuable hollow body 7 (see FIG. 1) lying behind the graduated filter 16 undergoes a deformation, which is detectable from a turning of the transmission disk serving as the graduated filter 16. The front view according to FIG. 2 reveals that the transmission disk 16 can be designed with three sectors 16.1, 16.2 and 16.3, which have a different degree of blackening in each case and therefore differently attenuate an infrared beam penetrating it at the light barrier 5. The light barrier 5 accordingly generates an electric signal 21, which corresponds to the optical density of the detected sectors 16.1, 16.2 or 16.3 and which can be used as a controlled variable for the rotational speed of the electromotive drive of the electrically drivable handpiece.

FIG. 3 shows that the component according to the invention is of quite a flat form and that the pressure chamber 10 for the driving-air connection is largely enclosed by the support part 1 and the plate 3 covering the latter. According to FIG. 3, the spindle 9, about which the graduated filter 16 can be turned when the hollow body 7 is actuated by pressure, lies in line with the spindle of the indicating disk 18.

The profile of the current intensity (I), and consequently the profile of the rotational speed at the electrically operable dental handpiece, in dependence on the driving-air pressure (P) is explained on the basis of FIG. 4 with the subfigures 5a to 5c.

With the configuration of a p/I analog transducer described in FIGS. 1 to 3, a characteristic profile which corresponds to the progressive characteristic profile designated in FIG. 4 by the reference numeral 27 can be achieved. In the range of driving-air pressures which lie below 1 bar, only small changes in the current intensity occur, while above pressures of 1 bar the changes in current intensity, and consequently the changes in rotational speed at the electrically operable dental handpiece, are greater.

Figure 5A:
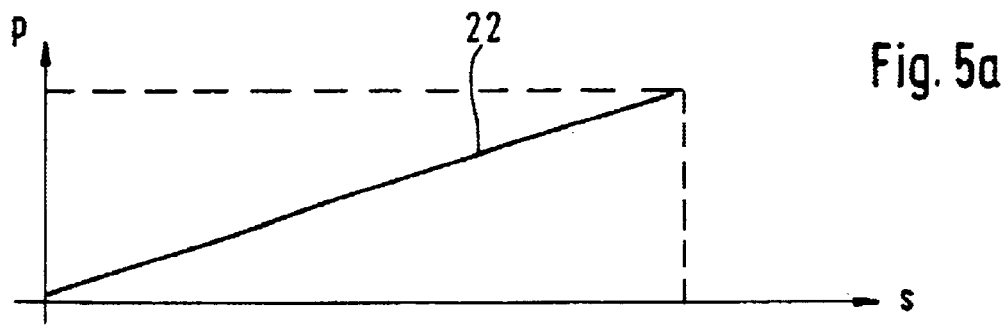
FIGS. 5a–c are graphic illustrations of the representation of several characteristics.
Figure 5B:
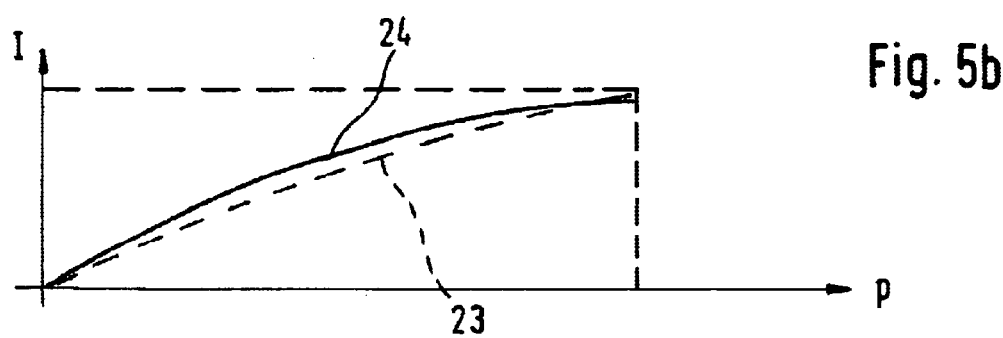
Figure 5C:
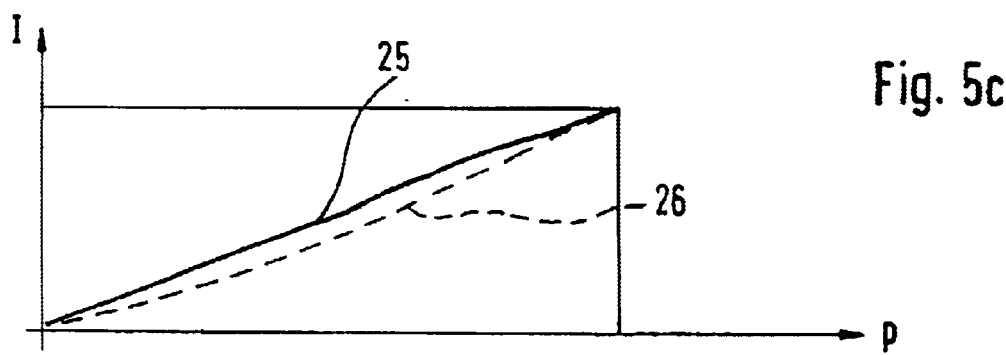

The calibration of the p/I analog transducer proposed according to the invention can be performed according to FIGS. 5a–c for example by means of a correction curve 26 stored in a micro-controller.

A linear pressure/displacement characteristic, as represented in FIG. 5a by the designation 22, can only be approximately reproduced by a linear characteristic 23 of the current intensity represented in FIG. 5b, plotted against the pressure (p). The ideal profile 24 of the current intensity can be achieved, however, by a correction curve 26 which is represented in FIG. 5c and can be performed as part of a calibration of the p/I analog transducer to be carried out on a micro-controller. With the correction values 26 stored in the micro-controller, a corrected profile 25 of the current intensity I over the pressure (p) can be calculated.

By the inclusion of the p/I analog transducer according to the invention, the method of controlling the rotational speeds of a pneumatically drivable handpiece and an electrically drivable handpiece via a shared foot-operated control achieves a characteristic profile which increases the operating convenience of an electrically operable handpiece by making its response to the control commands of the foot-operated control approximate the response of the pneumatically drivable handpiece to the control commands by the foot-operated control shared by the two handpieces.

Figure 6:
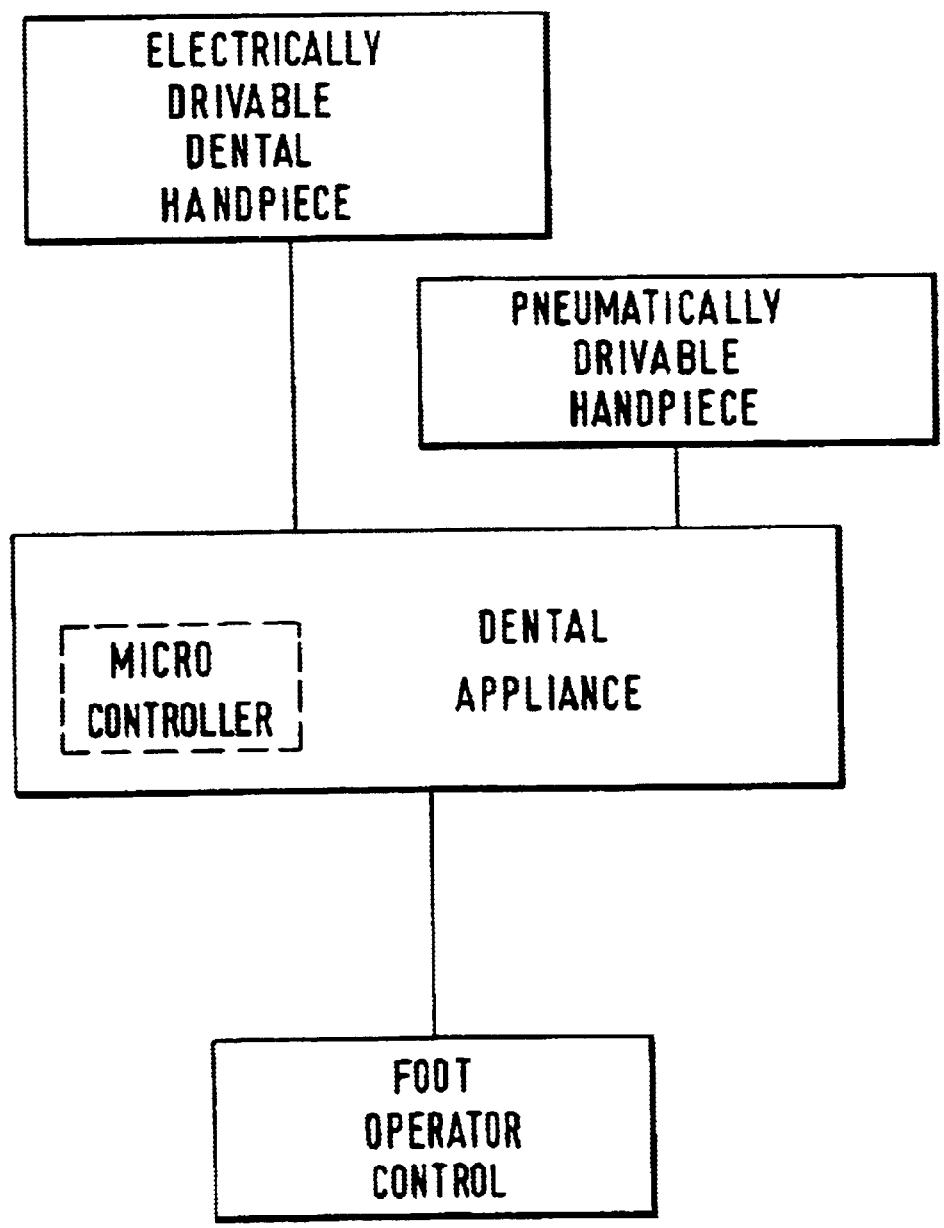
FIG. 6 is a schematic of a known dental appliance having basic features.

FIG. 6 illustrates, as a schematic diagram, a prior art dental appliance having electrically drivable and pneumatically drivable handpieces operated by a foot-control through a microcontroller.

What is claimed is:

1. A dental device with at least one electrically operable handpiece, the rotational speed of which can be influenced by a control element designed as a pneumatic foot-operated controller, the compressed air present at the output of the pneumatic control element influencing the control of the electric drive, wherein a graduated filter, mounted on a pneumatically actuated hollow body of the device, has regions which can be sensed by a light barrier generating an electric signal in dependence on the properties of the regions.

2. The dental device as claimed in claim 1, wherein the graduated filter comprises a transmission disk.

3. The dental device as claimed in claim 1, wherein properties of the regions comprise a surface finish thereof.

4. The dental device as claimed in claim 1, wherein properties of the regions comprise a degree of blackening thereof.

5. The dental device as claimed in claim 4, wherein the degree of blackening progresses continuously.

6. The dental device as claimed in claim 1, wherein the pneumatically actuable hollow body comprises a hollow spring.

7. The dental device as claimed in claim 1, wherein the pneumatically actuable hollow body comprises part of a p/I analog transducer.

8. The dental device as claimed in claim 1, wherein the regions of the graduated filter are enclosed by the light barrier generating the electric signal.

9. A method of controlling the rotational speeds of an electrically drivable dental handpiece and of a pneumatically drivable dental handpiece, both of which are mounted on a dental appliance and can be regulated in rotational speed thereof via a shared foot-operated control, comprising the steps of: applying driving air pressure to an input of a p/I analog transducer; deflecting a graduated filter by deforming a hollow body which is part of the p/I analog transducer; sensing the deflection of the graduated filter by a light barrier which is associated with the filter and which generates an electric signal; and determining current intensity of the p/I analog transducer in accordance with a progressive current/pressure characteristic.

10. The method as claimed in claim 9, having adjustable driving-air pressures from 0 to 4, wherein in the range of driving-air pressures of 0 to 1 bar, the current intensity which can be preset at the electric drive increases proportionately more weakly than in the case of driving-air pressures above 1 bar.

11. The method as claimed in claim 9, wherein the determination of the current intensity (I) of the p/I analog transducer is performed via a microcontroller, the correction curve being stored in a memory of the microcontroller.

* * * * *